United States Patent
Jossi et al.

(10) Patent No.: US 10,258,474 B2
(45) Date of Patent: Apr. 16, 2019

(54) ARTIFICIAL JOINT CUP (71) Applicant: JOSSI HOLDING AG, Islikon (CH)

(72) Inventors: Armin Jossi, Frauenfeld (CH);
Andreas Meyenhofer, Schlattingen (CH); Martin Schmidt, Warth (CH)

(73) Assignee: JOSSI HOLDING AG, Islikon (CH)

(*) Notice: Subject to any disclaimer, the term of this patent is extended or adjusted under 35 U.S.C. 154(b) by 1 day.

(21) Appl. No.: 15/506,369

(22) PCT Filed: Aug. 13, 2015

(86) PCT No.: PCT/EP2015/068665
§ 371 (c)(1),
(2) Date: Feb. 24, 2017

(87) PCT Pub. No.: WO2016/034387
PCT Pub. Date: Mar. 10, 2016

(65) Prior Publication Data
US 2017/0239056 A1    Aug. 24, 2017

(30) Foreign Application Priority Data

Sep. 1, 2014 (EP) .................... 14183090

(51) Int. Cl.
*A61F 2/34* (2006.01)
*A61F 2/30* (2006.01)

(52) U.S. Cl.
CPC ............ *A61F 2/34* (2013.01); *A61F 2/30767* (2013.01); *A61F 2/30771* (2013.01);
(Continued)

(58) Field of Classification Search
CPC .... A61F 2/34; A61F 2/30767; A61F 2/30771; A61F 2002/3082; A61F 2002/30822; A61F 2002/30836; A61F 2002/30843
See application file for complete search history.

(56) References Cited

U.S. PATENT DOCUMENTS 4,164,794 A * 8/1979 Spector ............... A61C 8/0012
427/195
5,538,532 A   7/1996 Keegel, Jr.
(Continued)

FOREIGN PATENT DOCUMENTS

DE    31 01 333 A1    12/1981
DE    31 30 732 A1    5/1983
(Continued)

OTHER PUBLICATIONS

International Search Report Corresponding to PCT/EP2015/068665 dated Oct. 22, 2015.
(Continued)

*Primary Examiner* — Christopher D. Prone
(74) *Attorney, Agent, or Firm* — Davis & Bujold PLLC; Michael J. Bujold (57) ABSTRACT An artificial joint cup, in particular a hip joint cup, for implanting in a cavity in a bone. The joint cup is, in particular, substantially in the form of a spherical dome cup, having a convex outer surface and a concave inner surface. In addition, the joint cup comprises an outer diameter and an inner diameter. The ratio of the difference between the outer diameter and the inner diameter, in relation to the outer diameter, is in a range of between 0.5 and 0.07, preferably between 0.3 and 0.075, particularly preferably between 0.2 and 0.1. The joint cup is manufactured from a ceramic material, and the convex outer surface has a micro-structuring.

14 Claims, 6 Drawing Sheets

(52) U.S. Cl.
CPC ... *A61F 2/3094* (2013.01); *A61F 2002/30011* (2013.01); *A61F 2002/3093* (2013.01); *A61F 2002/3098* (2013.01); *A61F 2002/30327* (2013.01); *A61F 2002/30769* (2013.01); *A61F 2002/30822* (2013.01); *A61F 2002/30827* (2013.01); *A61F 2002/30843* (2013.01); *A61F 2002/30968* (2013.01); *A61F 2002/30981* (2013.01); *A61F 2002/3446* (2013.01); *A61F 2002/3483* (2013.01); *A61F 2002/3496* (2013.01); *A61F 2310/00179* (2013.01); *A61F 2310/00203* (2013.01); *A61F 2310/00239* (2013.01); *A61F 2310/00299* (2013.01); *A61F 2310/00323* (2013.01); *A61F 2310/00407* (2013.01); *A61F 2310/00491* (2013.01); *A61F 2310/00544* (2013.01); *A61F 2310/00562* (2013.01); *A61F 2310/00634* (2013.01); *A61F 2310/00796* (2013.01)

(56) References Cited

U.S. PATENT DOCUMENTS

| | | | |
|---|---|---|---|
| 5,549,693 A † | 8/1996 | Roux | |
| 5,571,200 A | 11/1996 | Cohen et al. | |
| 5,702,473 A | 12/1997 | Albrektsson et al. | |
| 5,938,702 A † | 8/1999 | Lopez | |
| 6,231,612 B1 † | 5/2001 | Balay | |
| 6,319,285 B1 | 11/2001 | Chamier et al. | |
| 8,388,887 B2 † | 3/2013 | Gupta | |
| 8,702,806 B2 † | 4/2014 | Balay | |
| 9,198,761 B2 | 12/2015 | Gugler et al. | |
| 2001/0036530 A1* | 11/2001 | Noda | A61F 2/30767 428/104 |
| 2003/0050705 A1 † | 3/2003 | Cueille | |
| 2004/0117029 A1* | 6/2004 | Lewis | A61F 2/4684 623/22.28 |
| 2004/0153154 A1* | 8/2004 | Dinkelacker | A61C 8/0012 623/16.11 |
| 2006/0116774 A1 † | 6/2006 | Jones | |
| 2007/0142914 A1 † | 6/2007 | Jones | |
| 2009/0326671 A1 † | 12/2009 | Schofield | |
| 2010/0286789 A1 † | 11/2010 | Meridew | |
| 2011/0251698 A1 | 10/2011 | Gupta et al. | |
| 2013/0190889 A1 | 7/2013 | Li et al. | |

FOREIGN PATENT DOCUMENTS

| | | |
|---|---|---|
| DE | 251 074 A1 | 11/1987 |
| DE | 197 55 536 A1 | 6/1999 |
| DE | 697 17 586 T2 | 4/2003 |
| DE | 10 2012 105 070 A1 | 12/2013 |
| DE | 102012105070 A1 † | 12/2013 |
| EP | 1 025 815 A1 | 8/2000 |
| EP | 2338443 A1 † | 6/2011 |
| EP | 2 502 604 A1 | 9/2012 |
| WO | WO2009022911 A2 † | 2/2009 |
| WO | 2012/113690 A2 | 8/2012 |
| WO | WO2014008284 A1 † | 1/2014 |

OTHER PUBLICATIONS

Written Opinion Corresponding to PCT/EP2015/068665 dated Oct. 22, 2015.

\* cited by examiner
† cited by third party

ARTIFICIAL JOINT CUP

The present invention relates to an artificial joint cup according to the preamble of claim 1.

BACKGROUND OF THE INVENTION

When damage occurs to a joint socket, for example the acetabulum, of a patient, it is common practice to implant an artificial joint socket. Such joint sockets are known in various designs. On the one hand, they can have a multi-part design, for example composed of an outer joint cup (outer cup) and an inner joint cup (inner cup). The outer cup in this case serves for embedding the joint socket in a bone, while the inner cup, which is inserted into the outer cup, forms a bearing surface for a corresponding joint head. On the other hand, one-part artificial joint sockets with only one cup are known. Joint sockets of both types have been used in clinical practice for some time.

If a joint socket is implanted as a pre-assembled unit, for example composed of an outer cup and of an inner cup or with only one cup, it is referred to as a so-called monobloc socket. Joint sockets of this kind reduce the risk of an inner cup coming loose from the outer cup. They are very stable, but their design and the necessary thickness of the respective materials means that they are relatively bulky.

This has the result that, even in the case of quite minor damage to the natural joint socket, for example the acetabulum, of a patient, especially when the cartilage is damaged and the bone intact, quite a lot of material has to be removed when preparing the bone for the implantation. In young patients in particular, this means that, when preparing the bone to receive the artificial joint socket, quite a lot of bone substance is already lost at an early stage, and, consequently, there is no longer so much bone substance available if follow-up surgery proves necessary at a later stage.

A further problem with conventional joint cups is that, on account of the necessary wall thickness of the joint cup, the joint ball is relatively small by comparison with the natural joint. This has the disadvantage of altering the characteristics of the ball joint. Moreover, on account of the small joint ball, very high loads occur at points in the joint. Lastly, the thickness of the wall of artificial joint cups presents a problem, particularly in patients requiring the implantation of a very small joint cup.

EP 1 025 815 A1 discloses an artificial joint cup provided for implantation in a corresponding cavity in the bone of a patient and having a wall thickness of ca. 2.5 mm to 3 mm. Said joint cup is produced from metal, in particular a cobalt-chromium alloy. Moreover, both the inner surface and the outer surface of said joint cup can be coated with different materials.

However, in a joint cup of this kind, the small wall thickness means that the required mechanical stability of the cup structure can be achieved only with difficulty when using metal. Moreover, depending on the choice of the material for the joint head, the sliding behavior of the latter on the inner surface of the metallic cup presents a problem, as a result of which the inner surface of the joint cup in some cases has to be coated with a further non-metallic material. However, applying a particularly smooth coating to the inner surface of the joint cup can be achieved only with considerable effort. A further problem lies in embedding the cup in a stable position in a bone of a patient. A stable hold cannot always be ensured. Moreover, the cup material, in particular on the outer surface, is not always biocompatible.

SUMMARY OF THE INVENTION

The object of the invention is therefore to overcome the disadvantages of the prior art.

In particular, the object of the invention is to make available a joint cup which has a monobloc configuration and can be used in a hip bone with the least possible loss of bone material. However, a joint cup according to the invention should permit the use of a joint head that has substantially the same diameter as a natural joint head. The joint cup should also be able to be realized in a very small diameter and thus be suitable for implantation in especially small patients. However, the joint cup should ensure a very high level of mechanical stability. Furthermore, a joint cup according to the invention should be well tolerated by a patient and in particular should have a high degree of biocompatibility. Above all, however, it should be able to be anchored securely in a bone structure and, within a short period of time, establish a firm union with the bone of a patient.

These objects are achieved by a joint cup that has the features of claim 1.

The invention relates to an artificial joint cup, in particular a hip joint cup, for implanting in a cavity in a bone. The joint cup has in particular substantially the form of a spherical dome cup, having a convex outer surface and a concave inner surface. Moreover, the joint cup has an outer diameter (OD) and an inner diameter (ID). In this context, the outer diameter (OD) refers to the diameter of a ball whose surface has the same curvature as the mean curvature of the convex outer surface of a joint cup according to the invention. The inner diameter (ID) relates to the diameter of a ball whose surface corresponds to the concave inner surface of the joint cup that is present. The ratio of the difference (D) between the outer diameter (OD) and the inner diameter (ID) in relation to the outer diameter (OD) is here in a range between 0.5 and 0.07, preferably between 0.3 and 0.075, particularly preferably between 0.2 and 0.1.

In a cup with an outer diameter (OD) of 4.0 cm, this would correspond, in the case of a corresponding spherical dome cup, to a wall thickness in a range of between 10 mm and 1.4 mm, preferably between 6 mm and 1.5 mm, more preferably between 4 mm and 2 mm. In a cup with an outer diameter (OD) of 9.0 cm, the wall thickness would accordingly lie in a range of between 22.5 mm and 3.2 mm, preferably between 13.5 mm and 3.4 mm, more preferably between 9 mm and 4.5 mm.

The invention is characterized in that the joint cup is made of a ceramic material, and the convex outer surface has a macro-structuring.

By using ceramic as the cup material, it is possible to produce a very thin joint cup with a particularly high degree of mechanical strength. The loss of bone material when implanting a cup of this kind in a patient is therefore minimal. Moreover, a cup of this kind allows an artificial ball joint to be made available in which the joint head has substantially the same size as in a corresponding natural joint. This results in joint characteristics that are as natural as possible. Moreover, very high mechanical loads, as often occur in smaller joint balls, are avoided.

Furthermore, a cup of this kind is particularly well tolerated by the body and in particular has excellent biocompatibility. Through the choice of ceramic as cup material, the joint socket can be implanted in a bone of a patient without any problems, the outer surface of the cup forming a strong union with the bone structure within a short space of time.

A central role is played here by the macro-structuring on the convex outer surface. This macro-structuring significantly increases the outer surface area of the joint cup. This additionally promotes a strong union between the joint cup and the bone in which it is implanted.

The concave inner surface can form a bearing surface for a joint ball that is to be received in the joint cup. By virtue of this monobloc design, the cup does not require an inner cup (inlay), nor does the concave bearing surface have to be coated in the course of production. Traditional material combinations can be used for the bearing surface and the joint ball, thereby ensuring an optimal sliding behavior of the joint. Alternatively, however, the concave inner surface can also form a holding surface for an inner cup that is to be received in the joint cup. A suitably constructed joint socket can be implanted only as an outer cup or in monobloc form. This versatility of use means that a joint cup according to the invention can be employed in a wide range of medical indications.

The macro-structuring on the convex outer surface of the joint cup can comprise a multiplicity of structure elements. The latter can be delimited by depressions, preferably by material ablations, and measure from 0.3 mm to 3 mm. Depending on the surface structuring, very efficient manufacturing of a joint cup of this kind is possible, since the surface, for example after the production of a green body, can be cut away, ground, etched, sand-blasted, ablated by laser or worked by other methods involving removal of material. A further possibility is that the macro-structuring of the surface is already formed during the molding of the ceramic joint cup. In this connection, an example of a possible production method is slip casting. It is likewise possible for structure elements to be applied to a smoother surface.

However, said macro-structuring can also comprise a pore structure with a multiplicity of cavities that measure from 0.03 mm to 3 mm. A porous surface structure of this kind can be obtained, for example, by producing the joint cup from a porous ceramic material or by applying a porous outer ceramic layer onto a blank.

A macro-structuring of this kind may be suitable for inward growth of the trabecular structure of a bone. The trabecular structure, also called the substantia spongiosa, is a sponge-like system of fine trabeculae in the interior of a bone. As this bone structure becomes incorporated in the macro-structuring of the surface of the joint cup, a very strong connection (osseointegration) between joint cup and bone is permitted.

In a preferred embodiment of a joint cup according to the invention, depressions which separate structure elements in one row from each other can be arranged offset relative to each other in relation to depressions which separate structure elements in an adjacent row from each other. By virtue of this arrangement, surface structures can be created which facilitate the introduction of the implant into the bone. Furthermore, a surface structure is obtained which permits good anchoring of the implant in the bone. Moreover, forces acting on the implant are distributed optimally to the surrounding bone tissue.

The depressions, in particular the material ablations, which delimit the structure elements can also be formed by intersecting grooves of mutually opposite pitch. This surface structuring also permits good anchoring of the joint socket in the bone. Furthermore, a structuring of this kind can be applied to the surface of a joint socket in a very simple and cost-effective manner.

Said structure elements can be shaped as cubes, pyramids, tetrahedrons, wedges, polyhedrons or have the shape of an acute-angled pitched roof. The shape of the structure elements depends on the shape of the depressions, in particular on the removal of material. By suitable choice of the configuration, it is thus possible to create a large number of shapes of structure elements. In this way, the surface structuring can be adapted to the respective type of bone structure, and therefore, depending on the medical indication that is present, an ideal anchoring of the implant in the bone can be achieved.

The depressions, in particular the material ablations, can form concave surface areas, of which the curvature has a radius of curvature of at least 0.1 mm. This is particularly important in the production of the ceramic joint cup when the surface of a green body is machined before the sintering process. With radii of less than 0.1 mm, fractures can occur in the implant on account of the notch effect during the sintering.

The ceramic material from which the joint cup is made can have osteoconductive properties. In this context, the term osteoconductive refers to the fact that an osteoconductive material can form a supporting structure for the osteocytes, as a result of which the natural bone growth is promoted. Accordingly, an osteoconductive cup material made of ceramic supports the healing process of the bone after an implantation and promotes the formation of a stable connection between cup implant and the bone.

The ceramic material from which the joint cup is made can consist of an osteoconductive sintered oxide ceramic, preferably a zirconium oxide ceramic or an aluminum oxide/zirconium oxide mixed ceramic. Such materials are distinguished by excellent biocompatibility, good machinability and a high degree of mechanical strength.

The convex outer surface of the joint cup preferably has an osteoconductive coating. This makes it possible to choose the ceramic cup material purely according to criteria of mechanical strength and to achieve optimal osteoconductivity through the choice of a suitable coating material.

The osteoconductive coating can have a micro-structuring. Such a micro-structuring can, for example, comprise a pore structure with a multiplicity of cavities that measure from 0.003 mm to 0.3 mm.

By virtue of the stated micro-structuring, inter alia, the osteoconductive coating can additionally be osteointegrative. In this context, the term osteointegrative surface refers to a surface which can establish a direct functional and structural union with the organized living bone tissue. It is thus possible to achieve extremely firm anchoring of the implant in a bone provided for this purpose.

The osteoconductive and preferably also osteointegrative coating can consist of an osteoconductive metal, preferably an osteoconductive transition metal. Metallic coatings are particularly well suited to being applied to ceramic surfaces. Examples of possible coating methods are plasma coating, vapor phase deposition (chemical vapor deposition, physical vapor deposition), sputtering, sol-gel deposition, precipitation or electrophoresis. Thus, the osteoconductive coating can consist of platinum or of an element of the second or third transition group, preferably titanium, zirconium, niobium or tantalum. Materials of this kind are widely used in clinical practice for implants.

Moreover, the osteoconductive and preferably also osteointegrative coating can consist of hydroxyapatite or of an osteoconductive sintered oxide ceramic, preferably a zirconium oxide ceramic or an aluminum oxide/zirconium oxide mixed ceramic. Ceramic coatings are very suitable for said implant since they can be applied to the green body during the production of the implant, as a result of which they form a cohesive bond with it during the sintering process. Moreover, these materials are distinguished by excellent biocompatibility and by very good properties of osteoconduction and osseointegration.

The ceramic material from which the joint cup is made can consist of a sintered oxide ceramic, preferably an aluminum oxide ceramic, a zirconium oxide ceramic, or an aluminum oxide/zirconium oxide mixed ceramic. In the course of the production process, these materials can be worked, in particular coated, cost-effectively and efficiently. Moreover, they allow a joint cup to be made with a high level of precision, which joint cup has a high level of mechanical strength.

Furthermore, the ceramic material from which the joint cup is made can be chosen from a list consisting of titanium carbide ceramic, titanium oxycarbide ceramic, titanium nitride ceramic, titanium carbonitride ceramic, titanium aluminum nitride ceramic, titanium aluminum carbonitride ceramic, titanium zirconium nitride ceramic and silicon nitride ceramic. These materials are distinguished by being extremely hard, which gives the joint cup a very high level of rigidity and, in addition, can improve the sliding behavior of a joint ball on a concave bearing surface in a one-part joint cup.

Further advantages and individual features of the invention will become clear from the following description of a number of illustrative embodiments and from the figures, in which:

DESCRIPTION OF THE PREFERRED EMBODIMENTS

Figure 1:
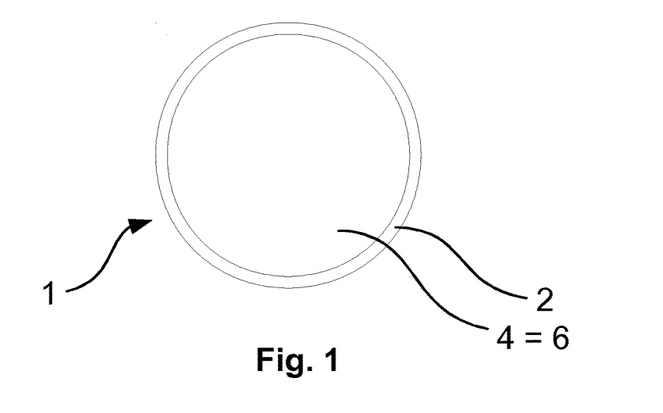
FIG. 1 shows a plan view of a joint cup according to the invention.

FIG. 1 shows a plan view of a one-part joint socket 1 with a joint cup according to the invention. Here, the concave bearing surface 4 at the same time also forms the bearing surface 6 for a joint ball that is to be inserted into the joint socket 1.

Figure 2:
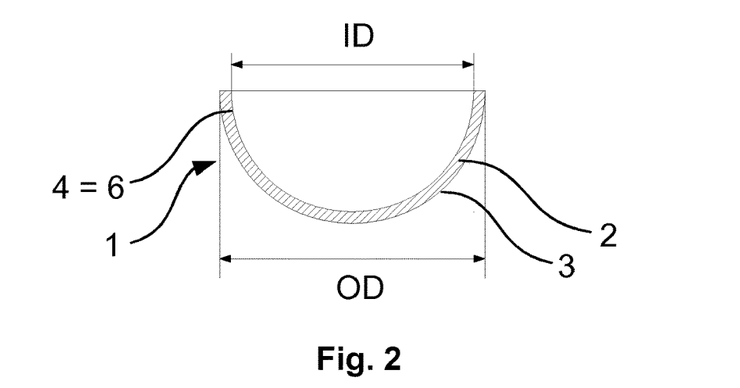
FIG. 2 shows a section through a joint cup according to FIG. 1.

FIG. 2 shows a section through a one-part joint socket 1 with a joint cup 2 according to the invention as per FIG. 1. This joint cup is in the form of a spherical dome cup with a convex outer surface 3 and a concave bearing surface 4. The joint cup has an outer diameter (OD) and an inner diameter (ID).

Figure 3:
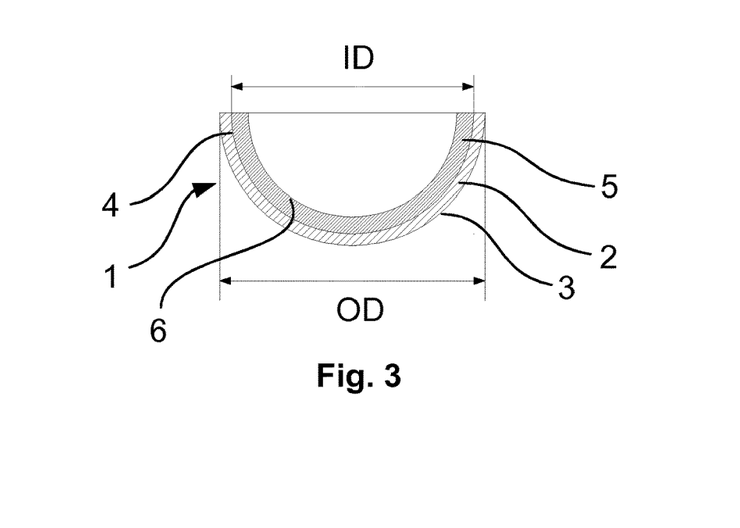
FIG. 3 shows a section through an alternative illustrative embodiment of a joint cup according to the invention.

FIG. 3 shows a section through a multi-part joint socket 1 with a joint cup 2 according to the invention into which an inner cup 5 is inserted. This inner cup 5 is rigidly connected to the concave inner surface 4 of the joint cup 2 and forms a bearing surface 11 for a joint ball that is to be inserted into the joint socket 1.

Figure 4:
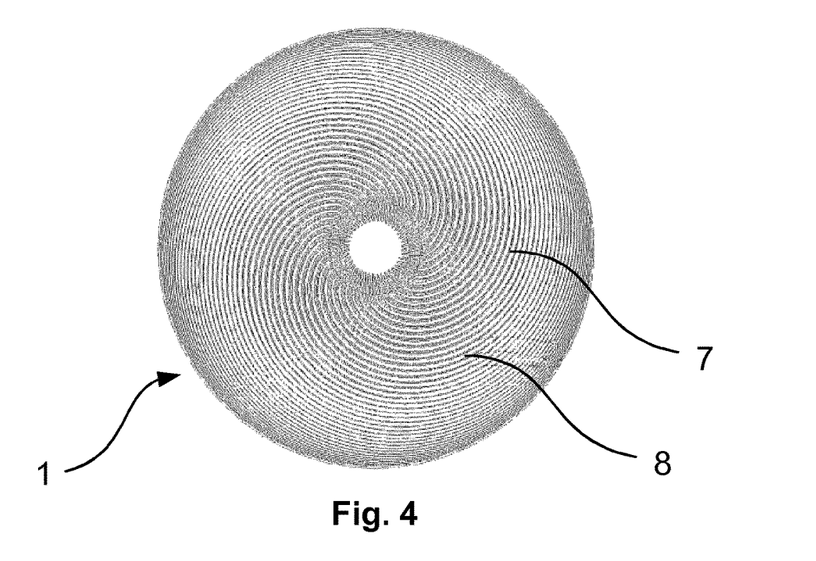
FIG. 4 shows a plan view of a joint cup according to the invention with spiral-shaped grooves.
Figure 5:
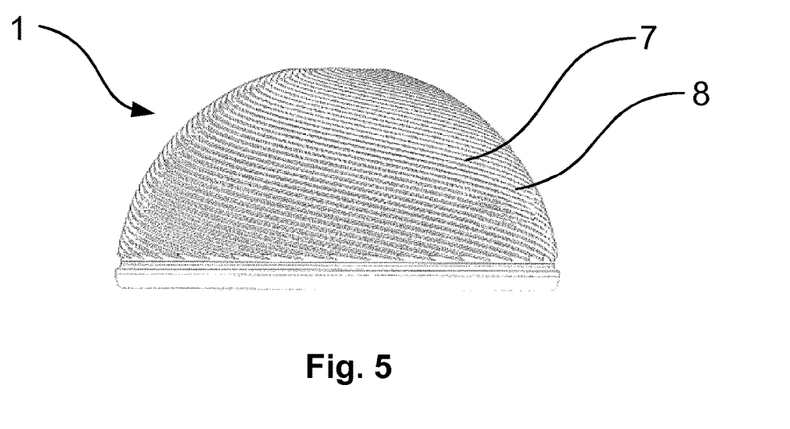
FIG. 5 shows a side view of a joint cup according to FIG. 4.

FIGS. 4 and 5 show a plan view and a side view of an illustrative embodiment of a joint cup 2 according to the invention. Here, the macro-structuring on the convex outer surface of the cup comprises a multiplicity of structure elements 7 which are delimited by depressions 8, in this case by spiral-shaped grooves.

Figure 6:
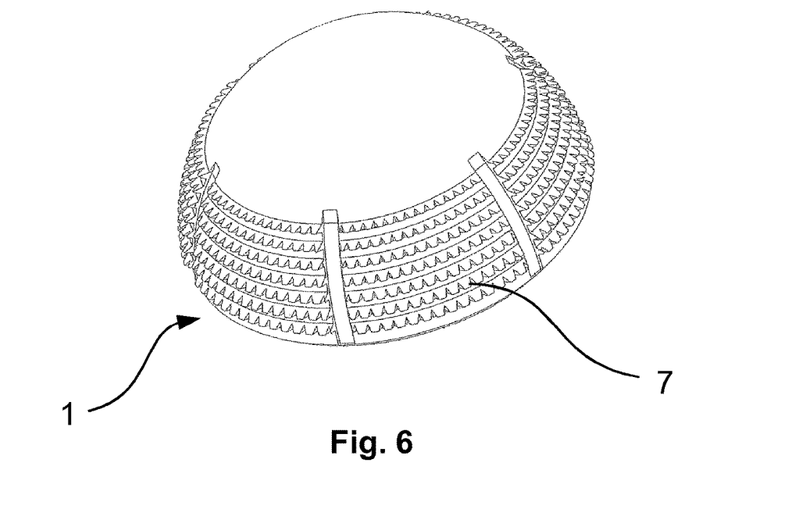
FIG. 6 shows a perspective view of a further embodiment of a joint cup according to the invention.
Figure 7:
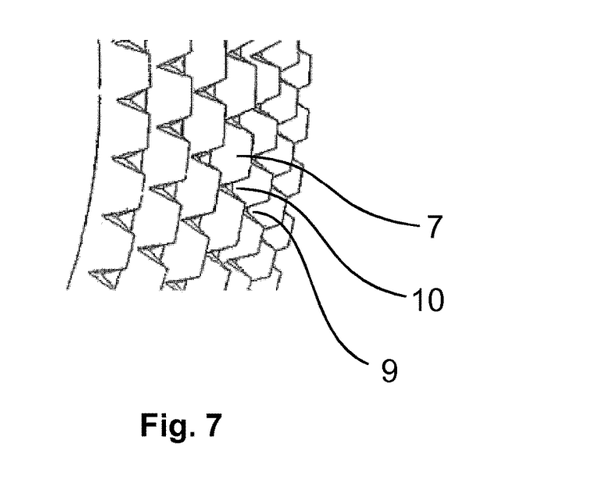
FIG. 7 shows a detailed view of the surface profile of a joint cup according to FIG. 6.

FIG. 6 shows a perspective view of an alternative embodiment of a joint socket 2 according to the invention. The surface profile of said joint socket 2 is shown enlarged in FIG. 7. It will be seen that the depressions 9, which separate the structure elements 7 in one row from each other, are arranged offset relative to each other in relation to depressions 10 which separate structure elements 7 in an adjacent row from each other.

Figure 8:
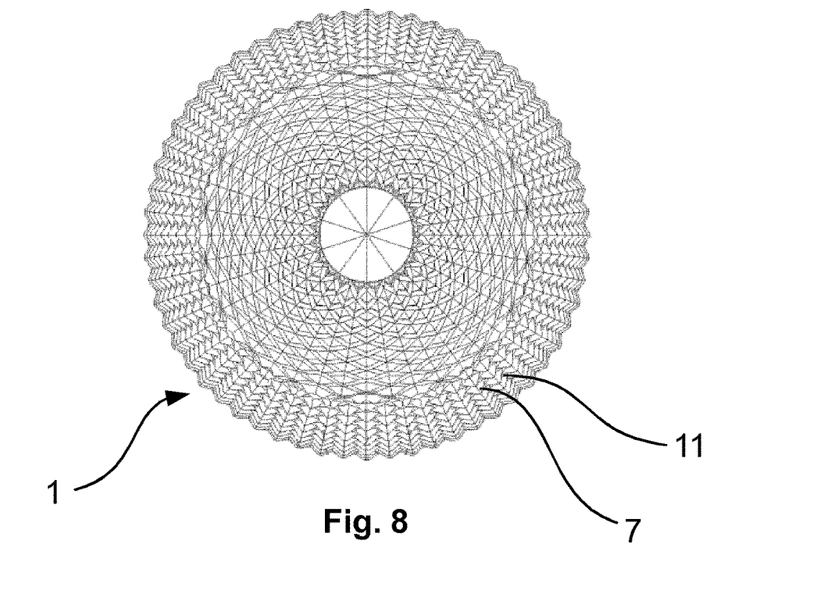
FIG. 8 shows a plan view of a further embodiment of a joint cup according to the invention with spiral-shaped grooves running in opposite directions.
Figure 9:
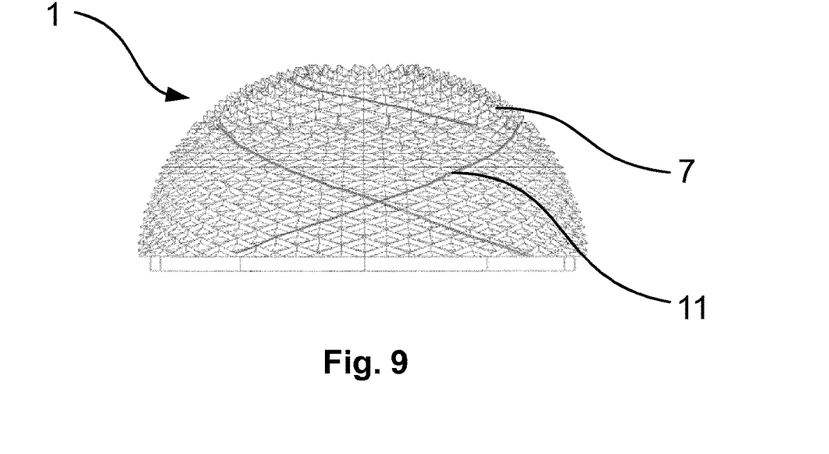
FIG. 9 shows a side view of a joint cup according to FIG. 8.

FIGS. 8 and 9 show a plan view and a side view of a further alternative embodiment of a joint socket 2 according to the invention. The depressions 11, which delimit the structure elements 7, are here formed by intersecting grooves with a mutually opposite pitch.

Figure 10:
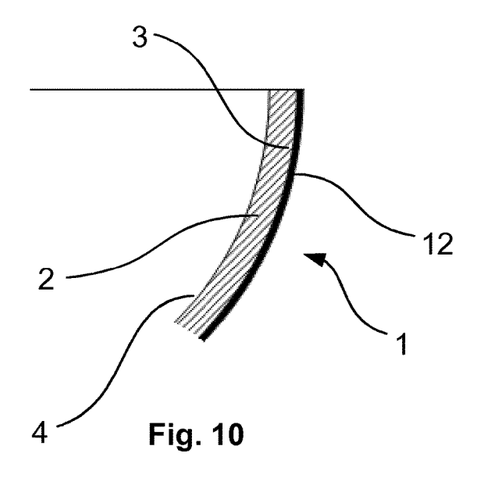
FIG. 10 shows a sectional image through a joint cup according to the invention with coating.

FIG. 10 shows a part of a section through a joint socket 2 according to the invention with a smooth convex outer surface 3. The joint cup 2 depicted has the shape of a spherical dome cup. The convex outer surface 3 has an osteoconductive coating 12. By contrast, the concave bearing surface 4 is uncoated.

Figures 11, 12:
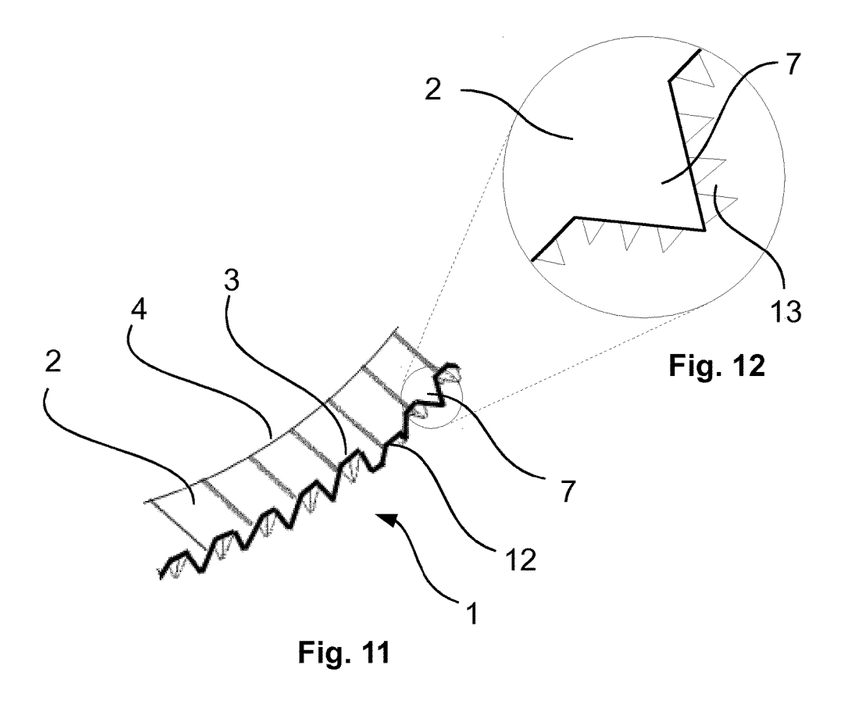
FIG. 11 shows a sectional drawing through an alternative embodiment of a joint cup according to the invention with coating.
FIG. 12 shows an enlarged detail of part of a sectional drawing through a joint cup according to FIG. 11.
Figure 13A:
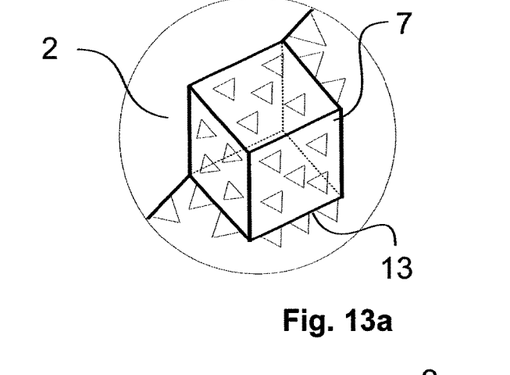
FIG. 13A diagrammatically shows a structure element in the shape of a cube.
Figures 13B, 13C:
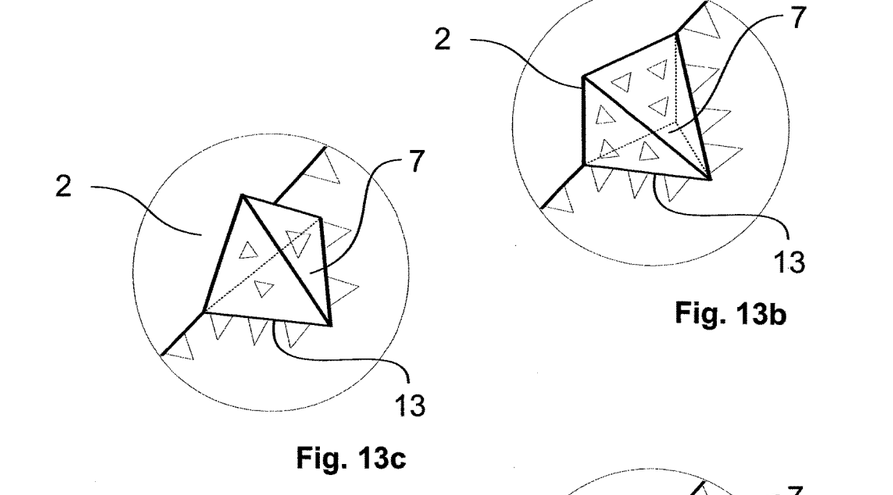
FIG. 13B diagrammatically shows a structure element in the shape of a pyramid.
FIG. 13C diagrammatically shows a structure element in the shape of a polyhedron.
Figure 13D:
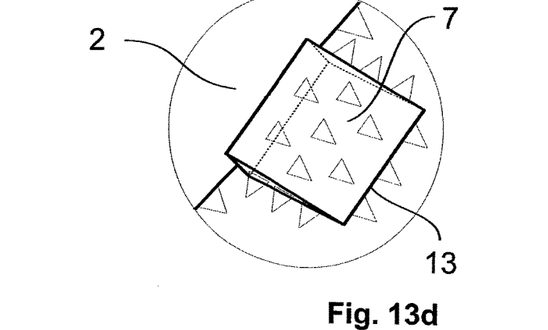
FIG. 13D diagrammatically shows a structure element in the shape of a wedge.

FIG. 11 shows a part of a section through a further alternative illustrative embodiment of a joint cup 2 according to the invention. In this case, the joint cup has a macro-structured outer surface 3. This outer surface 3 is provided with an osteoconductive coating 12. By contrast, the concave inner surface 4 on the inside of the spherical dome cup is also uncoated here.

FIG. 12 shows an enlarged detail of part of a section through a joint cup 2 according to the invention as per FIG. 11. It will be seen that an osteoconductive coating 12, which in turn has pores 13, is located on the structure elements 7 of the macro-structuring. By way of these pores, the surface can form a direct functional and structural union with the bone tissue.

FIGS. 13A, 13B, 13C and 13D diagrammatically shown a structure element shaped as a cube, a pyramid, a polyhedron and wedge, respectively.

The invention claimed is:

1. An artificial joint cup for implanting in a cavity in a bone having a convex outer surface and a concave inner surface, having an outer diameter and an inner diameter,
    wherein a ratio of a difference between the outer diameter and the inner diameter, in relation to the outer diameter, lies in a range of between 0.2 and 0.1,
    the joint cup is made of a ceramic material selected from the group consisting of titanium carbide ceramic, titanium oxycarbide ceramic, titanium nitride ceramic, titanium carbonitride ceramic, titanium aluminum nitride ceramic, titanium aluminum carbonitride ceramic, titanium zirconium nitride ceramic and silicon nitride ceramic, and
    the convex outer surface of the ceramic material has a macro-structuring comprising:
        a multiplicity of structure elements being delimited by depressions measuring form 0.3 mm to 3 mm, or
        a pore structure with a multiplicity of cavities that measure from 0.03 mm to 3 mm.

2. The joint cup as claimed in claim 1, wherein the concave inner surface forms a bearing surface for a joint ball that is to be received in the joint cup.

3. The joint cup as claimed in claim 1, wherein the concave inner surface forms a holding surface for an inner cup that is to be received in the joint cup.

4. The joint cup as claimed in claim 1, wherein the macro-structuring is suitable for inward growth of a trabecular structure of a bone.

5. The joint cup as claimed in claim 1, wherein depressions which separate structure elements in one row from each other, are arranged offset relative to each other in relation to depressions which separate structure elements in an adjacent row from each other.

6. The joint cup as claimed in claim 1, wherein the structure elements are shaped as cubes, pyramids, tetrahedrons, wedges or polyhedrons.

7. The joint cup as claimed in claim 1, wherein the ceramic material, from which the joint cup is manufactured, has osteoconductive properties.

8. The joint cup as claimed in claim 1, wherein the convex outer surface has an osteoconductive coating.

9. The joint cup as claimed in claim 8, wherein the osteoconductive coating is additionally osteointegrative.

10. The joint cup as claimed in claim 8, wherein the osteoconductive consists of an osteoconductive metal.

11. The joint cup as claimed in claim 10, wherein the osteoconductive coating consists of platinum or of an element of a second or third transition group.

12. The joint cup as claimed in claim 8, wherein the osteoconductive coating consists of hydroxyapatite or of an osteoconductive sintered oxide ceramic.

13. The joint cup as claimed in claim 8, wherein the ceramic material from which the joint cup is manufactured consists of a sintered oxide ceramic.

14. The joint cup as claimed in claim 1, wherein the osteoconductive coating has a micro-structuring comprising a pore structure with a multiplicity of cavities that measure from 0.003 mm to 0.3 mm.

* * * * *